(12) United States Patent
Uchimura et al.

(10) Patent No.: US 11,109,744 B2
(45) Date of Patent: Sep. 7, 2021

(54) THREE-DIMENSIONAL ENDOSCOPE SYSTEM INCLUDING A TWO-DIMENSIONAL DISPLAY IMAGE PORTION IN A THREE-DIMENSIONAL DISPLAY IMAGE

(71) Applicant: Sony Olympus Medical Solutions Inc., Tokyo (JP)

(72) Inventors: Sumihiro Uchimura, Tokyo (JP); Taihei Michihata, Kanagawa (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 302 days.

(21) Appl. No.: 16/273,247

(22) Filed: Feb. 12, 2019

(65) Prior Publication Data
US 2019/0290110 A1  Sep. 26, 2019

(30) Foreign Application Priority Data

Mar. 20, 2018 (JP) .............................. JP2018-052344

(51) Int. Cl.
| | |
|---|---|
| *A61B 1/00* | (2006.01) |
| *H04N 13/122* | (2018.01) |
| *A61B 1/04* | (2006.01) |
| *G02B 23/24* | (2006.01) |
| *A61B 90/30* | (2016.01) |
| *H04N 13/00* | (2018.01) |

(52) U.S. Cl.
CPC ...... *A61B 1/00193* (2013.01); *A61B 1/00009* (2013.01); *H04N 13/122* (2018.05); *A61B 1/00006* (2013.01); *A61B 1/04* (2013.01); *A61B 90/30* (2016.02); *G02B 23/2415* (2013.01); *H04N 2013/0092* (2013.01)

(58) Field of Classification Search
CPC ....... G02B 23/2415; H04N 2013/0092; H04N 13/122; H04N 13/156
See application file for complete search history.

(56) References Cited

U.S. PATENT DOCUMENTS

| | | | | |
|---|---|---|---|---|
| 2012/0271102 | A1* | 10/2012 | Katayama | ............... A61B 1/018 600/104 |
| 2014/0088353 | A1* | 3/2014 | Hayama | .................. A61B 1/018 600/104 |
| 2014/0221746 | A1* | 8/2014 | Katayama | .......... G02B 23/2415 600/111 |
| 2015/0018618 | A1* | 1/2015 | Ikeda | ................. G02B 23/2415 600/111 |
| 2015/0145953 | A1* | 5/2015 | Fujie | ......................... G06T 7/33 348/45 |
| 2016/0269713 | A1* | 9/2016 | Kasumi | .............. G02B 23/2484 |

FOREIGN PATENT DOCUMENTS

| | | | | |
|---|---|---|---|---|
| JP | | 2004065804 A | * 3/2004 | ......... A61B 1/00009 |
| WO | WO 2013/031512 A1 | | 3/2013 | |

* cited by examiner

*Primary Examiner* — John P Leubecker
(74) *Attorney, Agent, or Firm* — Xsensus LLP

(57) ABSTRACT

A three-dimensional endoscope system includes: an imaging unit configured to capture a first image and a second image having parallax with respect to each other; and an image generation unit configured to generate a display image for stereoscopic viewing by performing image processing on the first image and the second image captured by the imaging unit, wherein the image generation unit generates the display image based on the first image and a third image obtained by replacing a part of the second image with a part of the first image at a corresponding position.

14 Claims, 11 Drawing Sheets

THREE-DIMENSIONAL ENDOSCOPE SYSTEM INCLUDING A TWO-DIMENSIONAL DISPLAY IMAGE PORTION IN A THREE-DIMENSIONAL DISPLAY IMAGE

CROSS-REFERENCE TO RELATED APPLICATION

The present application claims priority to and incorporates by reference the entire contents of Japanese Patent Application No. 2018-052344 filed in Japan on Mar. 20, 2018.

BACKGROUND

The present disclosure relates to a three-dimensional endoscope system.

There is an increasing demand for stereoscopic observation in medical endoscope systems. Various methods are known as a stereoscopic endoscope system. For example, International Publication No. 2013/031512 discloses a stereoscopic endoscope system including: a rigid endoscope having optical systems for the left eye and the right eye; and two imaging units for individually capturing a left-eye image signal and a right-eye image signal based on light collected by each of the optical systems.

Meanwhile, the image for stereoscopic viewing described above brings about, on the near point side, a significant difference between the right-eye image and the left-eye image due to parallax. When this difference is excessive, image formation on the near point side would fail, leading to blurring of the image. The stereoscopic image having such blurring would increase visual strain for an operator to recognize the image.

SUMMARY

A three-dimensional endoscope system according to one aspect of the present disclosure includes: an imaging unit configured to capture a first image and a second image having parallax with respect to each other; and an image generation unit configured to generate a display image for stereoscopic viewing by performing image processing on the first image and the second image captured by the imaging unit, wherein the image generation unit generates the display image based on the first image and a third image obtained by replacing a part of the second image with a part of the first image at a corresponding position.

DETAILED DESCRIPTION

Figure 1:
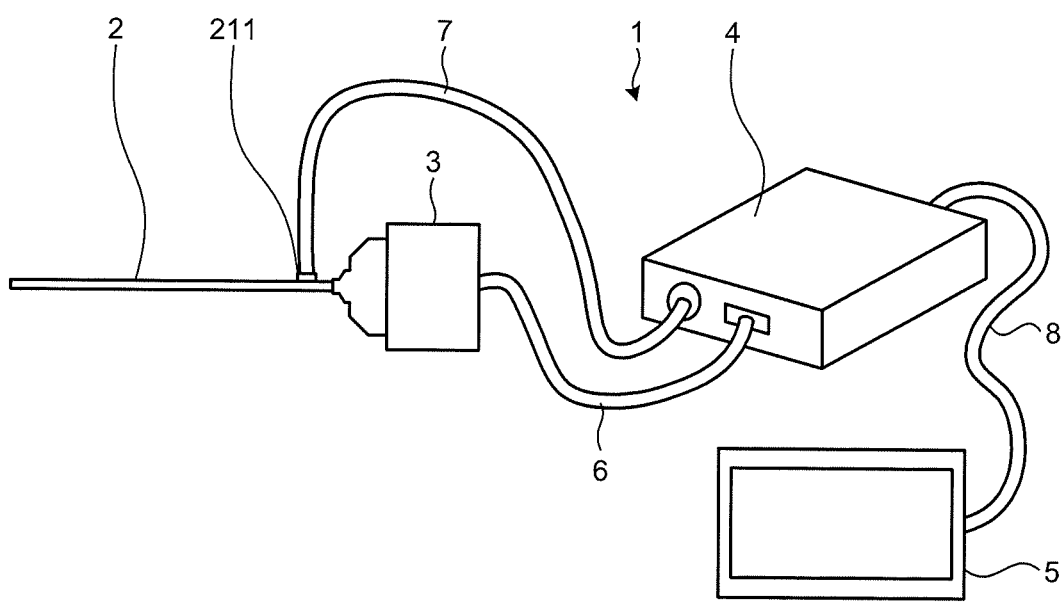
FIG. 1 is a diagram illustrating a schematic configuration of a medical endoscope system according to a first embodiment.

Hereinafter, a mode for carrying out the present disclosure (hereinafter referred to as "embodiment") will be described. In the embodiment, a medical endoscope system for capturing and displaying an image inside a subject such as a patient will be described as an example of a three-dimensional endoscope system according to the present disclosure. The present disclosure is not limited by this embodiment. In the description of the drawings, the identical reference numerals will be used to denote identical portions.

First Embodiment

FIG. 1 is a diagram illustrating a schematic configuration of a medical endoscope system 1 according to a first embodiment. The medical endoscope system 1 illustrated in the figure is a system for stereoscopically observing the inside of a living body. The medical endoscope system 1 includes: a rigid endoscope 2 having its a distal end portion inserted into a living body to collect light in the living body while illuminating the living body; a camera head 3 that captures light from the living body collected by the rigid endoscope 2 to generate two image signals having parallax with respect to each other; a control device 4 that controls operation of the camera head 3 and generates illumination light to be supplied to the rigid endoscope 2; a display device 5 connected to the control device 4 to display information such as an image; a transmission cable 6 that connects the camera head 3 with the control device 4 to transmit an electric signal or the like; a light guide cable 7 that connects the rigid endoscope 2 with the control device 4 to transmit illumination light; and a video cable 8 that connects the control device 4 with the display device 5 to transmit information such as an image. The rigid endoscope 2 and the camera head 3 constitute an imaging device 101.

Figure 2:
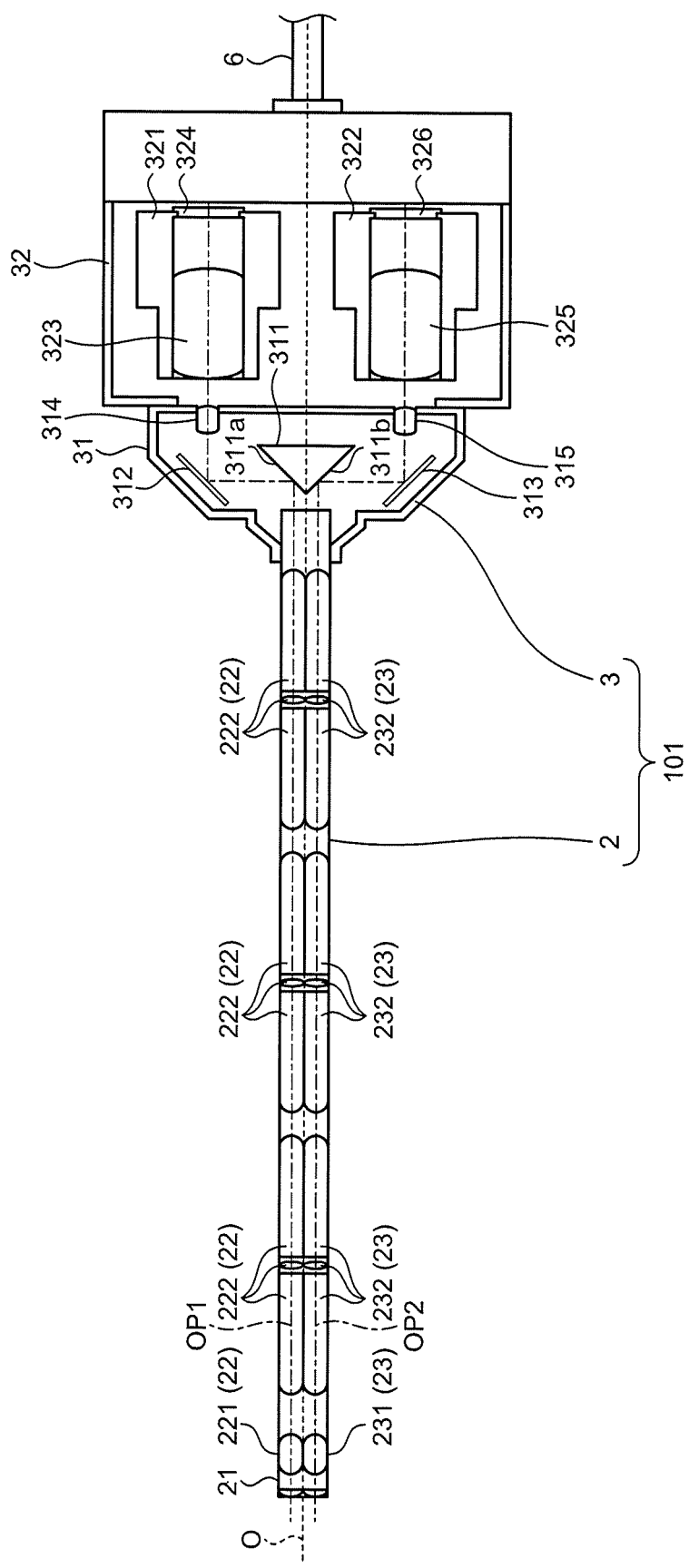
FIG. 2 is a view illustrating an internal configuration of a rigid endoscope and a camera head included in the medical endoscope system according to the first embodiment.

FIG. 2 is a view illustrating an internal configuration of the rigid endoscope 2 and the camera head 3. FIG. 2 is a view obtained by rotating the rigid endoscope 2 and the camera head 3 illustrated in FIG. 1 by 90 degrees about a longitudinal axis as a rotational axis.

First, the configuration of the rigid endoscope 2 will be described. The rigid endoscope 2 includes an insertion tube 21 having rigidity and an elongated shape; a first collecting optical system 22 and a second collecting optical system 23, arranged in parallel in the insertion tube 21. In addition, the rigid endoscope 2 includes an illumination optical system that transmits illumination light from an individual light source of the control device 4 to be applied to the living body. The rigid endoscope 2 is connected detachably and non-rotatably to the camera head 3.

The outer peripheral portion of the insertion tube 21 includes a mounting portion 211 for mounting a distal end portion of the light guide cable 7. The mounting portion 211 extends in a direction orthogonal to a center axis O of the insertion tube 21. The mounting portion 211 is connected to the illumination optical system inside the insertion tube 21. The illumination optical system guides light incident from the mounting portion 211 to the distal end of the insertion tube 21 and emits the light to the outside of the insertion tube 21. The mounting portion 211 is also referred to as a light guide post.

The first collecting optical system 22 includes a first objective optical system 221 and a first relay optical system 222 in order from the distal end portion side of the insertion tube 21. The first objective optical system 221 is provided at the distal end portion of the insertion tube 21 and collects first observation light from the observed region in the living body. The first relay optical system 222 guides the first observation light collected by the first objective optical system 221 to a proximal end (right end portion in FIG. 2) of the insertion tube 21. The first observation light is emitted from the proximal end of the insertion tube 21 to the camera head 3.

Similarly to the first collecting optical system 22, the second collecting optical system 23 includes a second objective optical system 231 and a second relay optical system 232 in order from the distal end side. Second observation light collected by the second collecting optical system 23 is emitted to the camera head 3 from the proximal end of the insertion tube 21. The second collecting optical system 23 is spaced apart from the first collecting optical system 22 in a radial direction of the insertion tube 21 inside the insertion tube 21. An optical axis OP2 of the second collecting optical system 23 is located at a position symmetrical to an optical axis OP1 of the first collecting optical system 22 with respect to the center axis O of the insertion tube 21. The size and focal position of an image circle of the second collecting optical system 23 are the same as those of the first collecting optical system 22, except that the second collecting optical system 23 has parallax.

Next, a configuration of the camera head 3 will be described with reference to FIG. 2. The camera head 3 includes: an optical path separating unit 31 that separates an optical path of the first observation light from the first collecting optical system 22 and an optical path of the second observation light from the second collecting optical system 23; and an imaging unit 32 that captures each of the first and second observation light to generate two image signals.

The optical path separating unit 31 includes: a triangular prism 311 that individually reflects the first and second observation light and changes their optical paths to opposite directions; and a pair of mirrors 312 and 313 that respectively reflect the first and second observation light reflected by the triangular prism 311 to direct their optical paths to be parallel to each other; and a pair of eyepiece optical systems 314 and 315 that respectively emit the first and second observation light reflected by the pair of mirrors 312 and 313, to the imaging unit 32.

The triangular prism 311 has a triangular prism shape having a right-angled isosceles triangle-shaped bottom. In the triangular prism 311, a first side surface 311a and a second side surface 311b, which are equal in area and orthogonal to each other, are disposed respectively at an angle of 45 degrees with the optical axis OP1 of the first collecting optical system 22 and the optical axis OP2 of the second collecting optical system 23, provided on the rigid endoscope 2 attached to the camera head 3. The first side surface 311a reflects the first observation light and bends its optical path 90 degrees to be directed to the upper side in FIG. 2. The second side surface 311b reflects the second observation light and bends the optical path by 90 degrees to be directed to the lower side in FIG. 2.

The mirror 312 and the mirror 313 are located symmetrically with respect to the center axis O of the insertion tube 21 of the rigid endoscope 2 connected to the camera head 3. The surface of the mirror 312 forms an angle of 45 degrees with respect to the direction in which the first observation light reflected by the first side surface 311a is incident, and reflects the first observation light in a direction parallel to the center axis O. The surface of the mirror 313 forms an angle of 45 degrees with respect to the incident direction of the second observation light reflected by the second side surface 311b, and reflects the second observation light in a direction parallel to the center axis O.

The eyepiece optical system 314 and the eyepiece optical system 315 are located symmetrically with respect to the center axis O of the insertion tube 21. The first observation light reflected by the mirror 312 passes through the eyepiece optical system 314, so as to be incident on the imaging unit 32. The second observation light reflected by the mirror 313 passes through the eyepiece optical system 315, so as to be incident on the imaging unit 32.

The imaging unit 32 includes: a first imaging unit 321 that captures the first observation light to generate an image signal (right-eye image signal); and a second imaging unit 322 that captures the second observation light to generate an image signal (left-eye image signal).

The first imaging unit 321 includes: a first imaging optical system 323 that collects the first observation light emitted from the eyepiece optical system 314; and a first imaging element 324 that opto-electrically converts the first observation light collected by the first imaging optical system 323 to generate a right-eye image signal. The first imaging optical system 323 is formed with one or more lenses movable along the optical axis OP1, and includes: an optical zoom mechanism (not illustrated) to change the angle of view under the control of the control device 4; and a focus mechanism (not illustrated) to change the focus. The first imaging element 324 is formed with an image sensor such as a charge coupled device (CCD) or complementary metal oxide semiconductor (CMOS).

The second imaging unit 322 includes: a second imaging optical system 325 that collects the second observation light emitted from the eyepiece optical system 315; and a second imaging element 326 that opto-electrically converts the second observation light collected by the second imaging optical system 325 to generate a left-eye image signal. The optical axis OP2 of the second imaging optical system 325 is parallel to the optical axis OP1 of the first imaging optical system 323. The configurations of the second imaging optical system 325 and the second imaging element 326 similar to those of the first imaging optical system 323 and the first imaging element 324, respectively. In the second imaging unit 322, the size of the imaging area is the same as the imaging area of the first imaging unit 321. The optical zoom mechanism and the focus mechanism of the second imaging optical system 325 are driven under the control of the control device 4.

Figure 3:
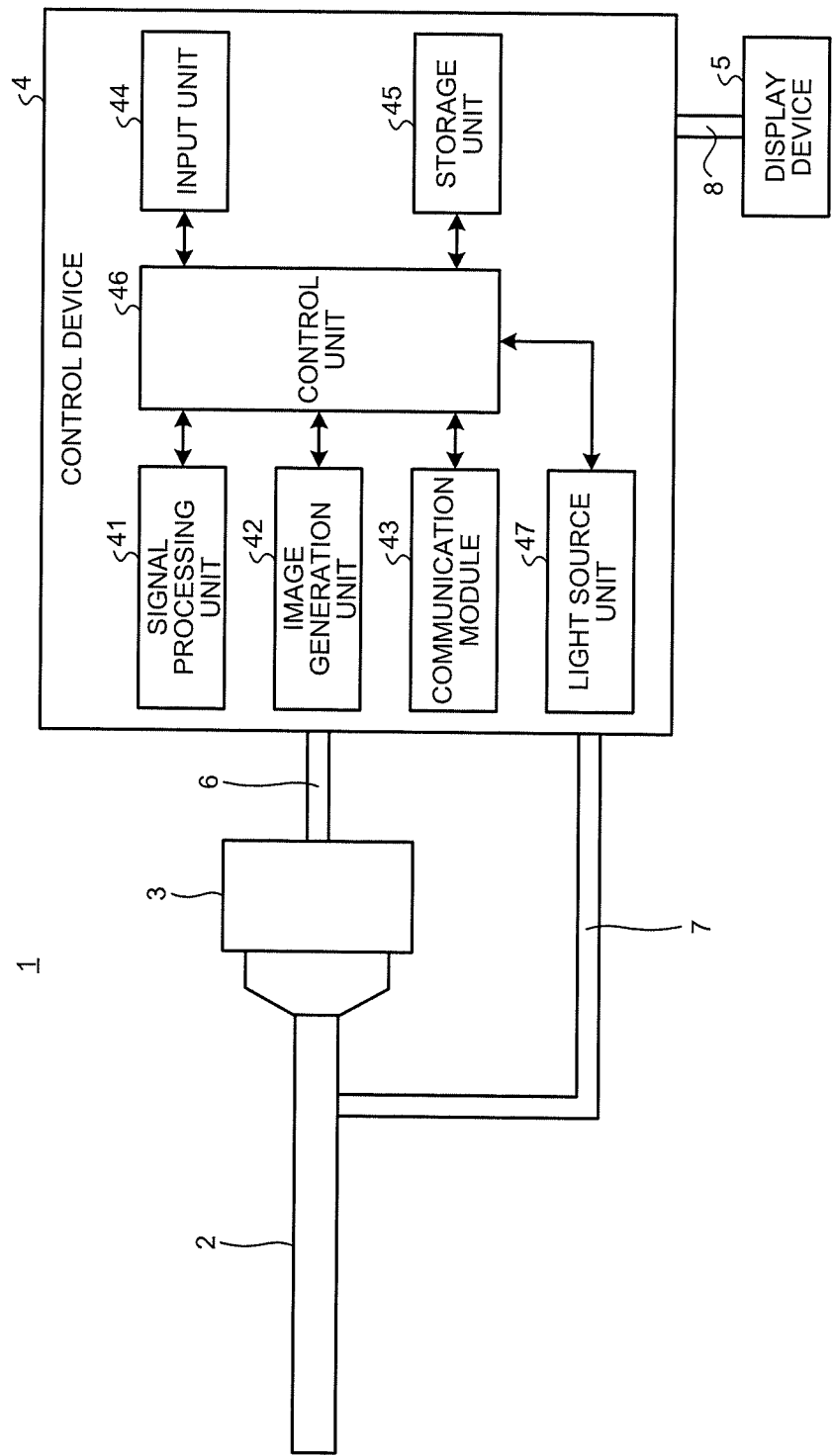
FIG. 3 is a block diagram illustrating a configuration of a control device included in the medical endoscope system according to the first embodiment.

Next, a configuration of the control device 4 will be described with reference to FIG. 3. FIG. 3 is a block diagram illustrating a configuration of the control device 4 included in the medical endoscope system 1 according to the first embodiment. The control device 4 receives the right-eye image signal generated by the first imaging unit 321 and the left-eye image signal generated by the second imaging unit 322, generates a display image signal (three-dimensional image signal), and outputs the generated image signal to the display device 5.

The control device 4 includes a signal processing unit 41, an image generation unit 42, a communication module 43, an input unit 44, a storage unit 45, a control unit 46, and a light source unit 47. The control device 4 may include a power supply unit (not illustrated) that generates a power supply voltage for driving the control device 4 and the camera head 3, supplies the generated voltage to individual portions of the control device 4 while supplying the generated voltage to the camera head 3 via the transmission cable 6.

The signal processing unit 41 performs signal processing such as noise removal and A/D conversion as necessary on the right-eye image signal and the left-eye image signal output from the camera head 3, so as to output a digitized imaging signals (pulse signal) to the image generation unit 42.

Furthermore, the signal processing unit 41 generates a synchronization signal and clocks for the camera head 3 and the control device 4. A synchronization signal (for example, a synchronization signal for instructing an imaging timing of the camera head 3) a clock (for example, a clock for serial communication) to the camera head 3 are transmitted to the camera head 3 by a line not illustrated. The camera head 3 is driven by the synchronization signal and the clock.

The image generation unit 42 performs image processing such as synchronization processing, white balance (WB) adjustment processing, gain adjustment processing, gamma correction processing, and format conversion processing, onto the right-eye image signal and the left-eye image signal. The image generation unit 42 causes the storage unit 45 to store the right-eye image signal and the left-eye image signal having undergone the image processing described above. The image generation unit 42 reads the right-eye image signal and the left-eye image signal having undergone image processing stored in the storage unit 45, so as to generate a three-dimensional image signal corresponding to the display format of the display device 5, as a display image signal. The image generation unit 42 clips a set area out of the imaging areas of the first imaging unit 321 and the second imaging unit 322, and combines the clipped right-eye image signal and the left-eye image signal to generate a three-dimensional image signal. In the first embodiment, the image generation unit 42 generates a three-dimensional image signal conforming to the top-and-bottom format.

Here, the image generation unit 42 may upconvert the clipped right-eye image signal and the left-eye image signal and then combine the upconverted images to generate a three-dimensional image signal. Specifically, in a case where an image has been clipped to a size corresponding to an image of standard definition (SD), the image may be upconverted to an image of high definition (HD). In another case where an image has been clipped to a size corresponding to the image of HD, the image may be upconverted to a 4K image with higher definition. In still another case where an image has been clipped to a size corresponding to the image of 4K, the image may be upconverted to an 8K image with higher definition. Here, an SD image is, for example, an image having a resolution of about 720 in the row direction and about 480 in the column direction. An HD image is an image having a resolution of, for example, 1920 in the row direction and around 1080 in the column direction. A 4K image is an image having a resolution of, for example, 3840 in the row direction and around 2160 in the column direction. An 8K image is an image having a resolution of, for example, 7680 in the row direction and 4320 in the column direction.

The communication module 43 outputs a signal from the control device 4 to the camera head 3. The communication module 43 also receives a signal from the camera head 3. That is, the communication module 43 is a relay device that outputs a signal from each of portions of the control device 4 to be output to the camera head 3 while outputting a signal input from the camera head 3 to each of portions of the control device 4.

The input unit 44 is a user interface that receives inputs of various operation signals related to the medical endoscope system 1 including the control device 4. The input unit 44 is implemented by using a user interface such as a keyboard, a mouse, a touch panel, or the like.

The storage unit 45 stores various programs needed for operation of the control device 4. The programs include a program used by the control device 4 to consolidate and control the medical endoscope system 1 as a master. The storage unit 45 is formed with a volatile memory such as a random access memory (RAM), or a nonvolatile memory such as a read only memory (ROM).

The control unit 46 controls operation of the medical endoscope system 1 including the control device 4. The control unit 46 controls operation of the signal processing unit 41, the image generation unit 42, and the light source unit 47, and controls operation of the camera head 3, so as to consolidate and control the medical endoscope system 1. The control unit 46 uses brightness information detected from an image to perform light source control, for example.

The light source unit 47 generates illumination light and supplies it to the light guide cable 7. The light source unit 47 includes: a light source formed with a light emitting diode (LED), a halogen lamp, or the like; a light source driver that drives the light source under the control of the control unit 46; and an emission optical system that collects light generated by the light source and emits the light to the light guide.

In the control device 4 having the above-described functional configuration, the signal processing unit 41, the image generation unit 42, and the control unit 46 are implemented by a general-purpose processor such as a central processing unit (CPU) or a dedicated integrated circuit, etc. that execute specific function, such as a Field Programmable Gate Array (FPGA).

The display device 5 is a three-dimensional display of an integral imaging method using a liquid crystal or an organic Electro Luminescence (EL) or a multi-eye method, configured to display a three-dimensional image based on a three-dimensional image signal generated by the control device 4.

The transmission cable 6 is used for individual communication between the camera head 3 and the control device 4. The transmission cable 6 is a metal cable that transmits an electric signal. The transmission cable 6 may be a fiber cable that transmits optical signals. In this case, the camera head 3 may include an electro-optical (E/O) conversion function and the control device 4 may include an opto-electric (O/E) conversion function. Alternatively, a metal cable and a fiber cable may be combined to form the transmission cable 6, and then, an image signal alone may be transmitted by an optical signal, and other signals may be transmitted by an electric signal. Furthermore, communication between the camera head 3 and the control device 4 may be performed wirelessly.

The light guide cable 7 is formed by a bundle of a plurality of optical fibers. The light guide cable 7 has one end connected to the control device 4 and the other end attached to the mounting portion 211 of the rigid endoscope 2, so as to guide the illumination light generated by the control device 4 to the light guide.

Figure 4:
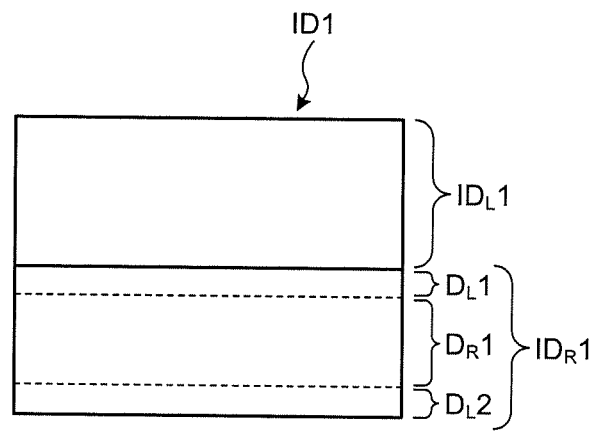
FIG. 4 is an example of a display image in the medical endoscope system according to the first embodiment, illustrating an image displayed on a display screen.

Subsequently, the three-dimensional image generation processing in the first embodiment will be described with reference to FIGS. 4 to 7. FIG. 4 is an example of a display image in the medical endoscope system according to the first embodiment, illustrating an image displayed on a display screen. As described above, the image generation unit 42 generates a three-dimensional image ID1 conforming to the top-and-bottom format (refer to FIG. 4). The three-dimensional image ID1 includes a left-eye image $ID_L1$ and a right-eye image $ID_R1$ aligned in an up-down direction. The left-eye image $ID_L1$ is an image obtained by clipping the set area from the left-eye image signal. The right-eye image $ID_R1$ includes: in its up-down direction, an intermediate area $D_R1$ obtained by clipping the set area from the right-eye image signal; and an upper area $D_L1$ and a lower area $D_L2$ respectively located at an upper and a lower portion of the intermediate area $D_R1$, having been clipped from the left-eye image signal. That is, the right-eye image $ID_R1$ is an image having a left-eye image, a right-eye image, and a left-eye image aligned in order from the top. The images of the upper area $D_L1$ and the lower area $D_L2$ of the right-eye image $ID_R1$ match the left-eye image $ID_L1$ when the right-eye image $ID_R1$ and the left-eye image $ID_L1$ are superimposed with each other. That is, the image of the upper area $D_L1$ of the right-eye image $ID_R1$ and the image of the corresponding position of the left-eye image $ID_L1$ are identical. In addition, the image of the lower area $D_L2$ of the right-eye image $ID_R1$ and the image of the corresponding position of the left-eye image $ID_L1$ are identical. The "position" here corresponds to the positional information (coordinates) attached to the array of the pixel values of the image. The "corresponding position" corresponds to a position that achieves matching when the left-eye image $ID_L1$ and the right-eye image $ID_R1$ are superimposed with each other. The image of the intermediate area $D_R1$ of the right-eye image $ID_R1$ is an image having parallax with respect to the left-eye image $ID_L1$ when the right-eye image $ID_R1$ and the left-eye image $ID_L1$ are superimposed with each other.

Figure 5:
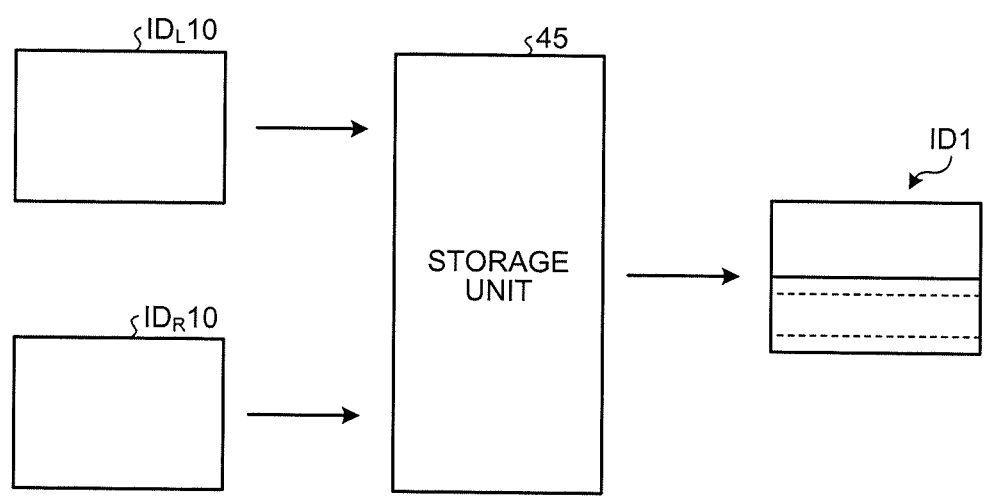
FIG. 5 is a view illustrating a method of reading an image signal in the medical endoscope system according to the first embodiment.
Figure 6:
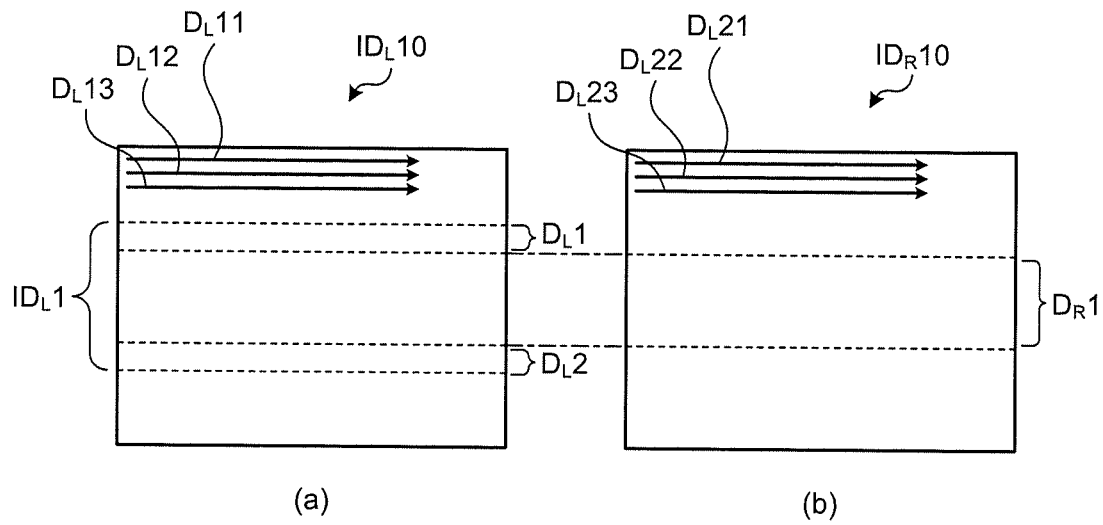
FIG. 6 is a view illustrating a method of reading an image signal in the medical endoscope system according to the first embodiment.

FIGS. 5 and 6 are views illustrating a method of reading an image signal in the medical endoscope system according to the first embodiment. The right-eye image signal (right-eye image $ID_R10$) and left-eye image signal (left-eye image $ID_L10$) having undergone image processing are temporarily stored in the storage unit 45 and read by the image generation unit 42 in accordance with a predetermined condition (refer to FIG. 5). Specifically, when generating the top-and-bottom format three-dimensional image ID1 illustrated in FIG. 4, the image generation unit 42 sequentially reads pixel values starting from the pixel corresponding to the upper left portion of FIG. 4 along the horizontal line of the pixels. Reading on the left-eye image $ID_L10$ when sequentially reading from the uppermost row is performed in the order starting from a first line $D_L11$ corresponding to the uppermost line to a second line $D_L12$, and then, the third line $D_L13$, and so on. Reading on the right-eye image $ID_R10$ when sequentially reading from the uppermost row is performed in the order starting from a first line $D_L21$ corresponding to the uppermost line to a second line $D_L22$, and then, the third line $D_L23$, and so on.

The image generation unit 42 first reads the left-eye image $ID_L1$ of the left-eye image $ID_L10$ (refer to (a) of FIG. 6), thereafter reads the upper area $D_L1$ of the left-eye image $ID_L10$, and thereafter reads the intermediate area $D_R1$ of the right-eye image $ID_R10$ (refer to (b) of FIG. 6), and finally reads the lower area $D_L2$ (refer to (a) of FIG. 6) of the left-eye image $ID_L10$. In this manner, target areas of individual images are sequentially read from the image signal stored in the storage unit 45, making it possible to generate the three-dimensional image ID1 as illustrated in FIG. 4.

Figure 7:
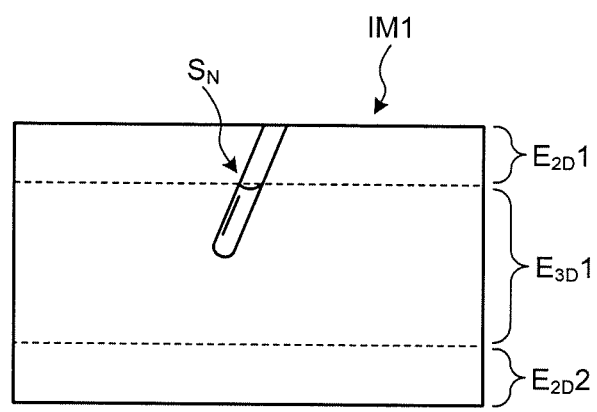
FIG. 7 is a view illustrating an example of a display image in the medical endoscope system according to first embodiment, illustrating an image visually recognized through polarized eyeglasses.

FIG. 7 is a view illustrating an example of a display image in the medical endoscope system according to the first embodiment, illustrating an image visually recognized through polarized eyeglasses. In the first embodiment, a three-dimensional image IM1 includes a three-dimensional display area $E_{3D}1$, in which an image of a treatment instrument is displayed as a three-dimensional image, and two-dimensional display areas $E_{2D}1$ and $E_{2D}2$. The three-dimensional display area $E_{3D}1$ and the two-dimensional display areas $E_{2D}1$ and $E_{2D}2$ individually extend in band shapes. The three-dimensional image IM1 includes the two-dimensional display areas $E_{2D}1$ and $E_{2D}2$ respectively arranged at upper and lower portions of the three-dimensional display area $E_{3D}1$. This result in displaying an image of a treatment instrument (hereinafter also referred to as a treatment instrument image) $S_N$ appearing in the three-dimensional image IM1 as a planar image (two-dimensional image) in the two-dimensional display area $E_{2D}1$, while as a stereoscopic image (three-dimensional image) in the three-dimensional display area $E_{3D}1$. Normally, the treatment instrument extends from the rigid endoscope 2 side toward the observation target. Accordingly, the outer edge side rather than the inner side is positioned closer to the near point, on the treatment instrument image $S_N$ of the three-dimensional image. In FIG. 7, the treatment instrument image $S_N$ enters from the upper direction of the three-dimensional image IM1. Accordingly, the upper the position is, the closer the image is to the near point, on the treatment instrument image $S_N$. Note that setting the area at least above the three-dimensional image IM1 to a two-dimensional display area would suppress blurring of the treatment instrument image $S_N$ on the near point side.

According to the above-described first embodiment, an object located on the near point side is displayed two-dimensionally at the time of three-dimensional display of an image. This configuration enables suppression of visual strain on the image for stereoscopic viewing.

In the first embodiment, the image generation unit 42 may detect the movement of the subject appearing in the left-eye image. When it is determined that the subject is moving, the image generation unit 42 may switch the display to a mixed display of two-dimensional and three-dimensional displays. In contrast, in a case where the image generation unit 42 determines that there is no movement in the subject, the image generation unit 42 generates a three-dimensional image including the left-eye images and the right-eye images (images formed with right-eye image signals alone) aligned with each other. Movement of the subject may be detected by using a known method such as pattern matching.

First Modification of First Embodiment

Figure 8:
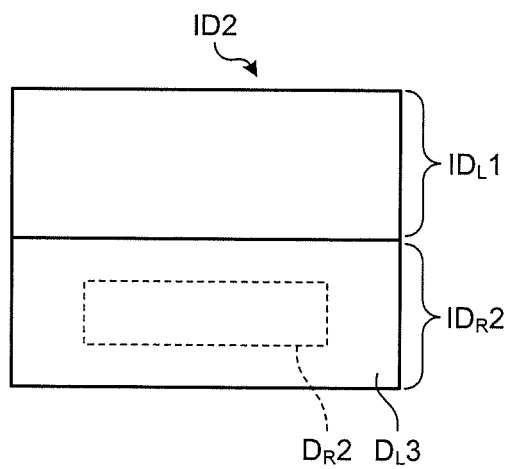
FIG. 8 is an example of a display image in the medical endoscope system according to the first modification of the first embodiment, illustrating an image displayed on the display screen.

Next, a first modification of the first embodiment will be described. FIG. 8 is an example of a display image in the medical endoscope system according to a first modification of the first embodiment, illustrating an image displayed on the display screen. While the above-described first embodiment is an example in which the upper area and the lower area in the right-eye image are replaced with the left-eye image, the first modification is an example in which an outer annular area along an outer periphery out of the right-eye image is to be replaced with the left-eye image.

As described above, the image generation unit 42 according to the first modification generates a three-dimensional image ID2 conforming to the top-and-bottom format. The three-dimensional image ID2 includes a left-eye image $ID_R1$ and a right-eye image $ID_R2$ aligned in an up-down direction. The right-eye image $ID_R2$ includes: a center area $D_R2$ obtained by clipping the set area from the right-eye image signal; and an outer annular area $D_L3$ located around the center area $D_R2$ having been clipped from the left-eye image signal. That is, the right-eye image $ID_R2$ is an image including a left-eye image arranged around a right-eye image. The image of the outer annular area $D_L3$ of the right-eye image $ID_R2$ matches the left-eye image $ID_L1$ when the right-eye image $ID_R2$ and the left-eye image $ID_L1$ are superimposed with each other. The image of the center area $D_R2$ of the right-eye image $ID_R2$ is an image having parallax with the left-eye image $ID_L1$ when the right-eye image $ID_R2$ and the left-eye image $ID_L1$ are superimposed onto each other.

According to the first modification, similarly to the above described first embodiment, an object located on the near point side is displayed two-dimensionally at the time of three-dimensional display of an image. This configuration enables suppression of visual strain on the image for stereoscopic viewing. In this first modification, it is possible to suppress visual strain regardless of the treatment instrument entry position on the outer periphery of the image.

Second Modification of First Embodiment

Figure 9:
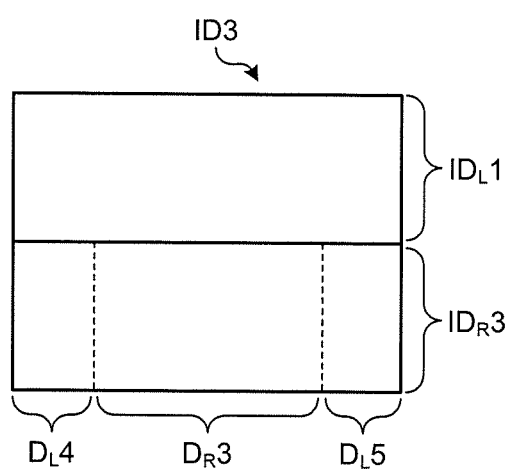
FIG. 9 is an example of a display image in the medical endoscope system according to a second modification of the first embodiment, illustrating an image displayed on the display screen.

Next, a second modification of the first embodiment will be described. FIG. 9 is an example of a display image in the medical endoscope system according to the second modification of the first embodiment, illustrating an image displayed on the display screen. While the above-described first embodiment is an example in which the upper area and the lower area in the right-eye image are replaced with the left-eye image, the second modification is an example in which a left area and a right area out of the right-eye image is to be replaced with the left-eye image.

As described above, the image generation unit 42 according to the second modification generates a three-dimensional image ID3 conforming to the top-and-bottom format. The three-dimensional image ID3 includes a left-eye image $ID_L1$ and a right-eye image $ID_R3$ aligned in an up-down direction. The right-eye image $ID_R3$ includes: in its horizontal direction, an intermediate area $D_R3$ obtained by clipping the set area from the right-eye image signal; and a left area $D_L4$ and a right area $D_L5$ respectively located at left and right portions of the intermediate area $D_R3$, having been clipped from the left-eye image signal. That is, the right-eye image $ID_R3$ is an image including a left-eye image at each of left and right sides of the right-eye image. The images of the left area $D_L4$ and the right area $D_L5$ of the right-eye image $ID_R3$ match the left-eye image $ID_L1$ when the right-eye image $ID_R3$ and the left-eye image $ID_L1$ are superimposed with each other. The image of the intermediate area $D_R3$ of the right-eye image $ID_R3$ is an image having parallax with the left-eye image $ID_L1$ when the right-eye image $ID_R3$ and the left-eye image $ID_L1$ are superimposed onto each other.

According to the second modification, similarly to the above described first embodiment, display of an object located on the near point side is to be displayed two-dimensionally at the time of three-dimensional display of an image. This configuration enables suppression of visual strain on the image for stereoscopic viewing. In this second modification, it is possible to suppress visual strain in a case where a treatment instrument enters from right and left sides of the image.

Second Embodiment

Figure 10:
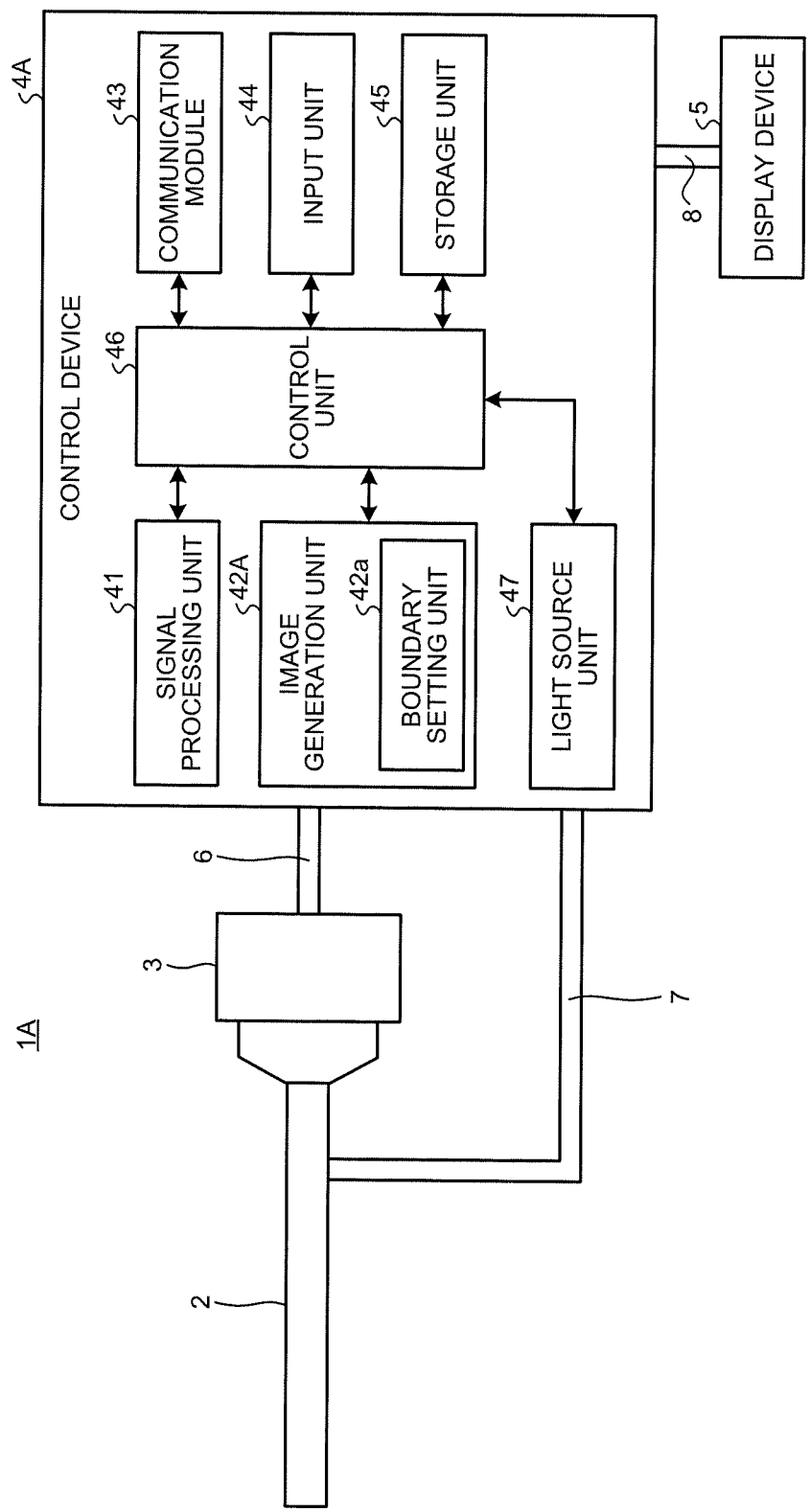
FIG. 10 is a diagram illustrating an internal configuration of a rigid endoscope and a camera head included in the medical endoscope system according to a second embodiment.

Next, a second embodiment will be described. FIG. 10 is a diagram illustrating an internal configuration of a rigid endoscope and a camera head included in the medical endoscope system according to a second embodiment. Note that the same reference numerals are used to designate the same components as those described above. In the second embodiment, the image generation unit includes a boundary setting unit as compared with the configuration of the above-described first embodiment.

A medical endoscope system 1A according to the second embodiment includes: the above-described rigid endoscope 2; the above-described camera head 3; a control device 4A that controls operation of the camera head 3 and generates illumination light to be supplied to the rigid endoscope 2; a display device 5 that displays information such as an image; a transmission cable 6 that connects the camera head 3 and the control device 4A to transmit an electric signal or the like; a light guide cable 7 that connects the rigid endoscope 2 and the control device 4A to transmit illumination light; and a video cable 8 that connects the control device 4A with the display device 5 to transmit information such as an image. Hereinafter, the control device 4A having a configuration different from that of the first embodiment will be described.

The control device 4A includes the signal processing unit 41, an image generation unit 42A, the communication module 43, the input unit 44, the storage unit 45, a control unit 46, and a light source unit 47. The control device 4A includes an image generation unit 42A in place of the image generation unit 42 of the control device 4 described above.

Similarly to the above-described image generation unit 42, the image generation unit 42A performs image processing on the right-eye image signal and the left-eye image signal. In addition, the image generation unit 42 causes the storage unit 45 to store the right-eye image signal and the left-eye image signal that have undergone the image processing described above. The image generation unit 42 reads the right-eye image signal and the left-eye image signal having undergone image processing stored in the storage unit 45, so as to generate a three-dimensional image signal corresponding to the display format of the display device 5, as a display image signal. The image generation unit 42 clips a set area out of the imaging areas of the first imaging unit 321 and the second imaging unit 322, and combines the clipped right-eye image signal and the left-eye image signal to generate a three-dimensional image signal. In the second embodiment, the image generation unit 42 generates a three-dimensional image signal conforming to the top-and-bottom format.

The image generation unit 42A includes a boundary setting unit 42a that sets a boundary between a two-dimensional display area to be two-dimensionally displayed and a three-dimensional display area to be three-dimensionally displayed. In a case where the two-dimensional display is to be performed based on the left-eye image, the boundary setting unit 42a detects the treatment instrument from the pixel value (luminance value) of the left-eye image, and sets a boundary between the two-dimensional display area and the three-dimensional display area based on the detected distal end position of the treatment instrument. In the second embodiment, the treatment instrument (treatment instrument image) corresponds to the subject.

Figure 11:
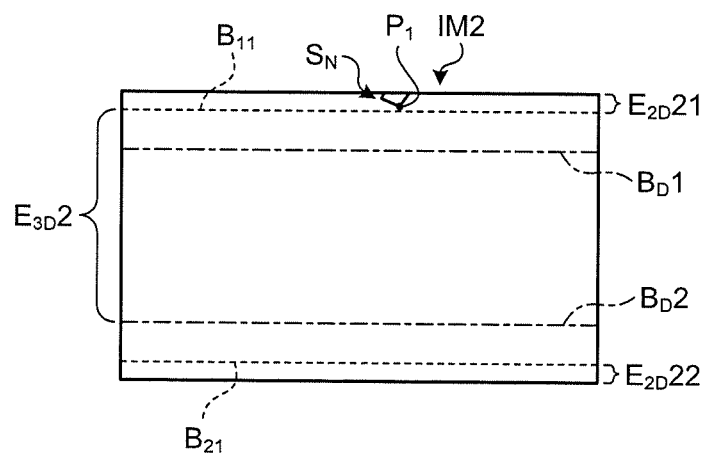
FIG. 11 is a view illustrating an example of a display image in the medical endoscope system according to the second embodiment, illustrating an image visually recognized through polarized eyeglasses.
Figure 12:
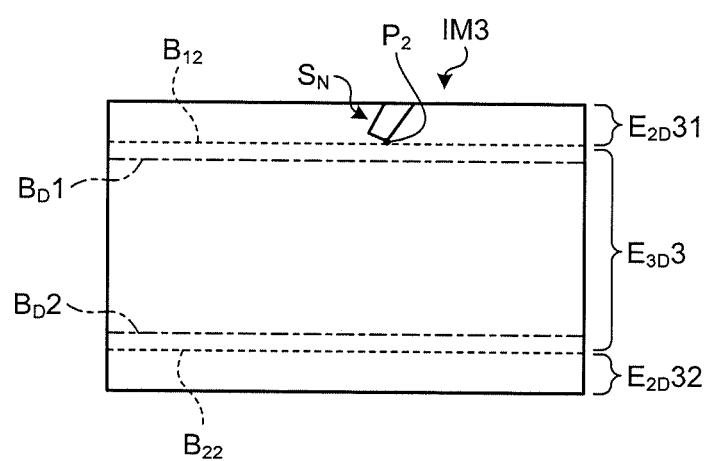
FIG. 12 is a view illustrating an example of a display image in the medical endoscope system according to the second embodiment, illustrating an image visually recognized through polarized eyeglasses.
Figure 13:
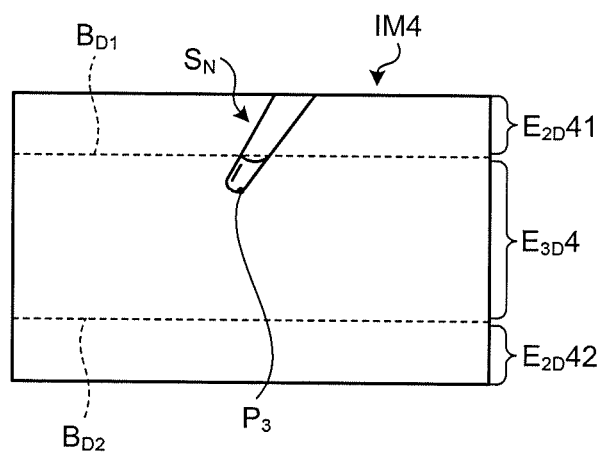
FIG. 13 is a view illustrating an example of a display image in the medical endoscope system according to the second embodiment, illustrating an image visually recognized through polarized eyeglasses.

FIGS. 11 to 13 are views illustrating an example of a display image in the medical endoscope system according to the second embodiment, illustrating an image visually recognized through polarized eyeglasses. When the treatment instrument (treatment instrument image) enters the three-dimensional image, the boundary setting unit 42a detects the distal end position of the treatment instrument from the luminance value of the left-eye image. For example, as illustrated in FIG. 11, when the treatment instrument image $S_N$ enters a three-dimensional image IM2, the boundary setting unit 42a detects a distal end position $P_1$ of the treatment instrument $S_N$ based on the luminance value. The distal end position $P_1$ detected here is the position of an end portion located at the centermost side in the vertical direction (up-down direction) of the image. After detection of the distal end position $P_1$, the boundary setting unit 42a sets boundaries $B_{11}$ and $B_{21}$ passing through the distal end position $P_1$ and extending in the horizontal direction (left-right direction). The boundary $B_{11}$ is a boundary between the two-dimensional display area and the three-dimensional display area at the top of the image. The boundary $B_{21}$ is a boundary between the two-dimensional display area and the three-dimensional display area at the bottom of the image. With this configuration, a three-dimensional display area $E_{3D}2$ and two-dimensional display areas $E_{2D}21$ and $E_{2D}22$ with the boundaries $B_{11}$ and $B_{21}$ defined as their boundaries are set in the three-dimensional image IM2. Here, boundaries $E_D1$ and $B_D2$ illustrated in FIG. 11 indicate a lower limit of the upper portion and an upper limit of the lower portion, respectively.

The vertical direction and the horizontal direction correspond to the vertical direction and the horizontal direction of the pixel arrangement. While the second embodiment sets the lower boundary $B_{21}$, it is allowable to simply set the boundary $B_{11}$ directly related to the treatment instrument image $S_N$.

The boundary setting unit 42a detects the distal end position of the treatment instrument image $S_N$ at preset intervals. When the boundary setting unit 42a determines that the distal end position has changed to cause the treatment instrument image $S_N$ to further enter the image from the state illustrated in FIG. 11, the boundary setting unit 42a changes the setting of the boundary (refer to FIG. 12). The boundary setting unit 42a detects the distal end position of the treatment instrument image $S_N$ from the luminance value of the left-eye image. The boundary setting unit 42a detects the distal end position $P_2$ of the treatment instrument image $S_N$ based on the luminance value in a three-dimensional image IM3. After detection of the distal end position $P_2$, the boundary setting unit 42a sets boundaries $B_{12}$ and $B_{22}$ passing through the distal end position $P_2$ and extending in the horizontal direction. With this configuration, a three-dimensional display area $E_{3D}3$ and two-dimensional display areas $E_{2D}31$ and $E_{2D}32$ with the boundaries $B_{12}$ and $B_{22}$ defined as their boundaries are set in the three-dimensional image IM3.

Here, in a case where the detected distal end position is located on the center side beyond the boundaries $B_{D1}$, and $B_{D2}$, the boundary setting unit 42a sets the boundary between the three-dimensional display area and the two-dimensional display area as the boundaries $B_D1$, and $B_D2$ (refer to FIG. 13). With this configuration, a three-dimensional display area $E_{3D}4$ and two-dimensional display areas $E_{2D}41$ and $E_{2D}42$ with the boundaries $B_D1$ and $B_D2$ defined as their boundaries are set in a three-dimensional image IM4.

According to the above-described second embodiment, an object located on the near point side is displayed two-dimensionally at the time of three-dimensional display of an image. This configuration enables suppression of visual strain on the image for stereoscopic viewing.

In the second embodiment, the boundary between the two-dimensional display area and the three-dimensional display area is changed in accordance with the entering degree of the treatment instrument. Therefore, when there is no object entering the near point side, it is possible to display the whole image three-dimensionally. In this manner, the second embodiment makes it possible to display an image accommodating the strain on the operator.

First Modification of Second Embodiment

Figure 14:
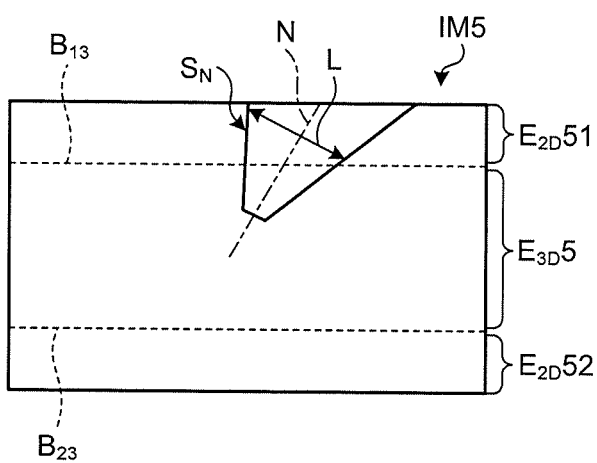
FIG. 14 is a view illustrating an example of a display image in the medical endoscope system according to a first modification of the second embodiment, illustrating an image visually recognized through polarized eyeglasses.

Next, a first modification of the second embodiment will be described. FIG. 14 is a view illustrating an example of a display image in the medical endoscope system according to the first modification of the second embodiment, illustrating an image visually recognized through polarized eyeglasses. While the second embodiment described above is an example in which the boundary is set in accordance with the distal end position of the treatment instrument image $S_N$, the first modification switches between three-dimensional display, and mixed display of two- and three-dimensional displays, based on diameter of the treatment instrument image $S_N$ appearing on the image. The configuration of the medical endoscope system according to first modification is the same as that of the medical endoscope system 1A described above. Hereinafter, processing different from the processing of the second embodiment will be described.

The boundary setting unit 42a according to the first modification detects a longitudinal axis N of the treatment instrument image $S_N$ from the luminance value of the left-eye image. The boundary setting unit 42a detects the longitudinal axis N of the treatment instrument image $S_N$ based on the contour of the treatment instrument image $S_N$, the present entrance direction of the treatment instrument, for example. Thereafter, the boundary setting unit 42a calculates a length L of the treatment instrument image $S_N$ in a direction orthogonal to the detected longitudinal axis N. The length L is, for example, a maximum value among the lengths calculated for a plurality of points set along the longitudinal axis N direction. This length L represents the diameter of the treatment instrument image $S_N$ in the image. The larger the length L, the more toward the near point the treatment instrument is to the rigid endoscope 2.

After calculating the length L, the boundary setting unit 42a determines whether to set the boundary between the two-dimensional display area and the three-dimensional display area based on the length L. In a case where the calculated length L exceeds a preset value, the boundary setting unit 42a sets the boundary between the two-dimensional display area and the three-dimensional display area. In the case illustrated in FIG. 14, the boundary setting unit 42a sets preset boundaries $B_{13}$ and $B_{23}$. The boundary $B_{13}$ is the boundary between the two-dimensional display area and the three-dimensional display area at the top of the image. The boundary $B_{23}$ is the boundary between the two-dimensional display area and the three-dimensional display area at the bottom of the image. With this configuration, a three-dimensional display area $E_{3D}5$ and two-dimensional display areas $E_{2D}51$ and $E_{2D}52$ with the boundaries $B_{13}$ and $B_{23}$ defined as their boundaries are set in a three-dimensional image IM5. In contrast, in a case where the calculated length L is a preset value or less, the boundary setting unit 42a sets the whole image as a three-dimensional display area.

In the first modification, the boundary between the two-dimensional display area and the three-dimensional display area is set in accordance with the proximity level of the treatment instrument. Therefore, when there is no object entering the near point side, it is possible to display the whole image three-dimensionally. In this manner, the first modification makes it possible to display an image accommodating the strain on the operator.

While the first modification is an example in which the preset boundary is set as the boundary between the two-dimensional display area and the three-dimensional display area, a boundary may be set in accordance with the distal end position of the treatment instrument image $S_N$.

Second Modification of Second Embodiment

Figure 15:
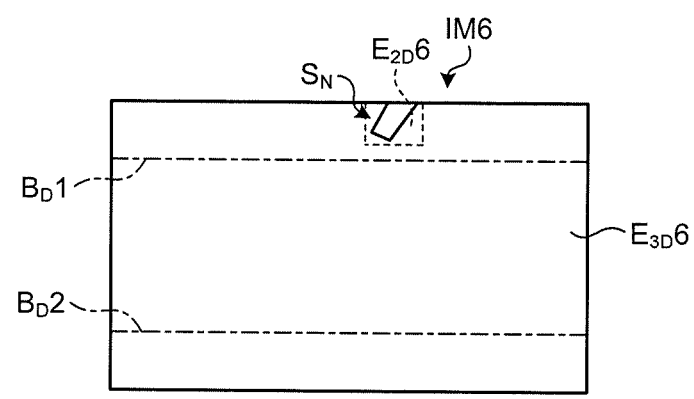
FIG. 15 is a view illustrating an example of a display image in the medical endoscope system according to a second modification of the second embodiment, illustrating an image visually recognized through polarized eyeglasses.

Next, a second modification of the second embodiment will be described. FIG. 15 is a view illustrating an example of a display image in the medical endoscope system according to the second modification of the second embodiment, illustrating an image visually recognized through polarized eyeglasses. While the second embodiment described above is an example in which the boundary extending in the horizontal direction is set in accordance with the distal end position of the treatment instrument image $S_N$, the second modification simply displays a partial area including the treatment instrument image $S_N$ appearing on the image, as the two-dimensional image. The configuration of the medical endoscope system according to second modification is the same as that of the medical endoscope system 1A described above. Hereinafter, processing different from the processing of the second embodiment will be described.

The boundary setting unit 42a according to the second modification extracts a contour of the treatment instrument image $S_N$ from the luminance value of the left-eye image. The contour may be extracted by using a known method such as edge detection. The boundary setting unit 42a sets a rectangular area spaced from the contour of the extracted treatment instrument image $S_N$ by a preset length, as the two-dimensional display area. That is, the boundary setting unit 42a sets boundaries, namely a boundary spaced from the distal end position of the treatment instrument image $S_N$ by a predetermined distance and extending in the horizontal direction, and two boundaries individually spaced from the treatment instrument image $S_N$ by a predetermined distance in the left and right direction of the treatment instrument image $S_N$ and extending in the vertical direction. The distal end position of the treatment instrument image $S_N$ may be detected from contours, luminance values, or the like. With this configuration, a three-dimensional display area $E_{3D}6$ and a rectangular two-dimensional display area $E_{2D}6$ are set in a three-dimensional image IM6. Note that a rectangular area circumscribing the treatment instrument image $S_N$ may be set as the three-dimensional display area. In a case where the distal end position of the treatment instrument image $S_N$ exceeds the boundary $B_D1$ as upper/lower limits, this boundary $B_D1$ is set as the boundary with the two-dimensional area.

In the second modification, the boundary between the two-dimensional display area and the three-dimensional display area is set in accordance with the contour of the treatment instrument. Therefore, it is possible to set a minimum display area including the object on the near point side as two-dimensional display area. In this manner, the first modification enables suppression of the strain on the operator, while enabling setting of a wider area as the three-dimensional display area as compared with the second embodiment or the like.

Note that an extracted contour of the treatment instrument may be set as the two-dimensional display area in the second modification.

Third Modification of Second Embodiment

Next, a third modification of the second embodiment will be described. While the second embodiment described above is an example in which the boundary is set in accordance with the distal end position of the treatment instrument image $S_N$, the third modification switches between three-dimensional display, and mixed display of two- and three-dimensional displays, based on a distance between the rigid endoscope 2 and an observed region. The configuration of the medical endoscope system according to the third modification is the same as that of the medical endoscope system 1A described above. Hereinafter, processing different from the processing of the second embodiment will be described.

The boundary setting unit 42a according to the third modification measures the distance between the rigid endoscope 2 and the observed region (for example, the treatment instrument image $S_N$) from the luminance value of the left-eye image. The distance between the rigid endoscope 2 (light receiving surface) and the observed region may be measured by using a known method. For example, driving the focus mechanism leads to acquisition of a focus evaluation value from signal detection information (contrast or frequency component) obtained at individual lens positions (focal positions), and then, the lens position having the largest focus evaluation value is determined as a focus position. The focal length is calculated based on this focus position (lens position). This focal length is defined as the distance between the rigid endoscope 2 and the observed region.

After measuring the distance, the boundary setting unit 42a sets the boundary between the two-dimensional display area and the three-dimensional display area based on the measured distance. For example, the boundary setting unit 42a sets a boundary such that the longer the distance, the larger the two-dimensional display area becomes.

In the third modification, the boundary between the two-dimensional display area and the three-dimensional display area is set based on the distance to be measured. Accordingly, it is possible to switch between the three-dimensional display, and a mixed display of two-dimensional display and three-dimensional display, in accordance with the presence or absence of the object located on the near point side.

Fourth Modification of Second Embodiment

Figure 16:
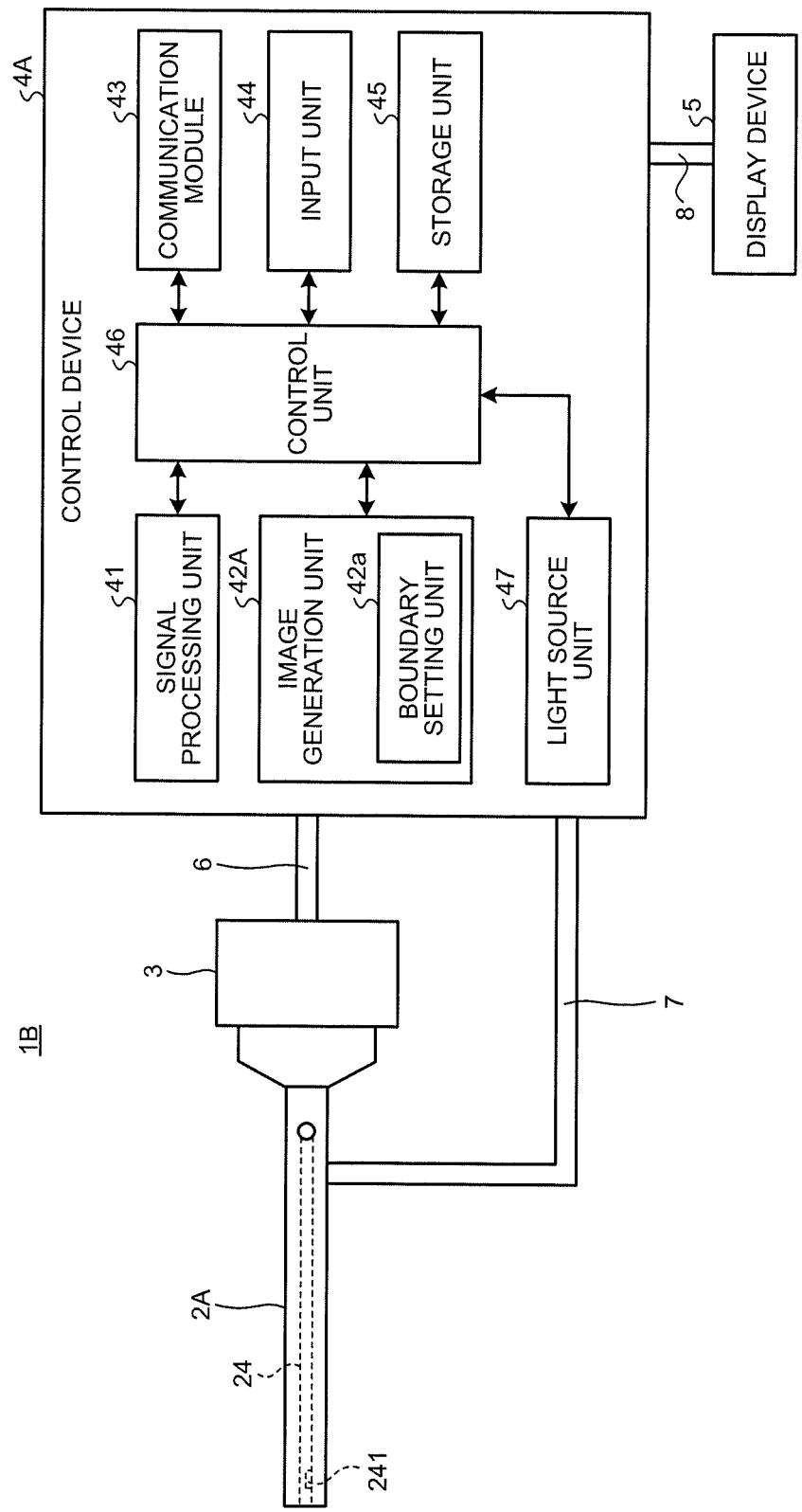
FIG. 16 is a diagram illustrating an internal configuration of a rigid endoscope and a camera head included in the medical endoscope system according to a fourth modification of the second embodiment.

Next, a fourth modification of the second embodiment will be described. FIG. 16 is a diagram illustrating an internal configuration of a rigid endoscope and a camera head included in the medical endoscope system according to a fourth modification of the second embodiment. Note that the same reference numerals are used to designate the same components as those described above. While the second embodiment described above is an example in which the boundary is set in accordance with the distal end position of the treatment instrument image $S_N$, the fourth modification includes a sensor on the rigid endoscope 2 and switches between three-dimensional display, and mixed display of two- and three-dimensional displays, based on a result of detection of the treatment instrument by the sensor. The configuration of the medical endoscope system according to the fourth modification is the same as that of the medical endoscope system 1A described above. Hereinafter, processing different from the processing of the second embodiment will be described.

A medical endoscope system 1B according to the fourth modification includes: the above-described rigid endoscope 2A; the above-described camera head 3; a control device 4A that controls operation of the camera head 3 and generates illumination light to be supplied to the rigid endoscope 2A; a display device 5 that displays information such as an image; a transmission cable 6 that connects the camera head 3 and the control device 4A to transmit an electric signal or the like; a light guide cable 7 that connects the rigid endoscope 2A and the control device 4A to transmit illumination light; and a video cable 8 that connects the control device 4A with the display device 5 to transmit information such as an image. Hereinafter, the rigid endoscope 2A having a configuration different from that of the second embodiment will be described.

In addition to the configuration of the rigid endoscope 2 described above, the rigid endoscope 2A includes a treatment instrument channel 24 through which the treatment instrument is inserted and extended from the distal end. The treatment instrument channel 24 includes, on its distal end, a sensor 241 for detecting the passage of the treatment instrument. The sensor 241 may be implemented by a known sensor such as an optical sensor, a magnetic detection sensor, or the like. The boundary setting unit 42a according to the fourth modification sets the boundary between the two-dimensional display area and the three-dimensional display area based on the detection result (signal value) of the sensor. When the boundary setting unit 42a determines that the treatment instrument has passed through the distal end of the treatment instrument channel 24 based on the detection value of the sensor, the boundary setting unit 42a switches to mixed display of two-dimensional and three-dimensional displays. The setting of the boundary may be performed, as described above, by setting a preset boundary, or setting the boundary by detecting the distal end position or contour of the treatment instrument.

In the fourth modification, the boundary between the two-dimensional display area and the three-dimensional display area is set based on the detection result of the sensor provided in the treatment instrument channel 24. Accordingly, it is possible to switch between the three-dimensional display, and a mixed display of two- and three-dimensional displays based on prediction of the object to enter on the near point side.

In addition, the rigid endoscope 2A having the treatment instrument channel 24 as the fourth modification has an advantage that the extending direction of the treatment instrument is known. Accordingly, the longitudinal axis N of the treatment instrument image $S_N$ in first modification may be easily set to with reference to the extending direction. At this time, the extending direction of the treatment instrument matches the longitudinal axis N. In this manner, the fourth modification may be applied to other embodiments and modifications.

While the above is description of the modes for carrying out the present disclosure, the present disclosure should not be limited by only the embodiments described above. In the above-described embodiment, the control device 4 performs signal processing or the like. Alternatively, however, signal processing or the like may also be performed on the camera head 3 side.

While the first and second embodiments described above are an example in which at least a part of the outer edge side of the image is two-dimensionally displayed. Alternatively, however, in a case where the image on the near point side of the subject is present in the center of the image, it is also allowable to display the center area including the image on the near point side of the subject as a two-dimensional image and may display the outer periphery of the center area as a three-dimensional image.

Moreover, while the first and second embodiments described above are an example of generating a three-dimensional image signal conforming to the top-and-bottom format. The present disclosure, however, is not limited to this. For example, the three-dimensional image signal may be generated based on other formats such as a line by line format, a side by side format, and a frame sequential format.

As described above, the three-dimensional endoscope system according to the present disclosure is useful for suppressing visual strain caused by viewing a stereoscopic image.

According to the present disclosure, it is possible to suppress the visual strain in viewing a stereoscopic image.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:
1. A three-dimensional endoscope system comprising:
circuitry configured to
capture a first image and a second image having parallax with respect to each other;

perform image processing on the first image and the second image; and generate a display image for stereoscopic viewing based on the first image and a third image obtained by replacing a first part of the second image with a first part of the first image at a first corresponding position and a second part of the second image with a second part of the first image at a second corresponding position, the second part being spaced from the first part such that the display image includes a three-dimensional display image between two separate two-dimensional display images.

2. The three-dimensional endoscope system according to claim 1, wherein a boundary between the second image and the first and second parts of the first image in the third image is preset.

3. The three-dimensional endoscope system according to claim 1, wherein the circuitry is configured to set a boundary between the second image and the first image in the third image in accordance with a subject appearing in the first image.

4. The three-dimensional endoscope system according to claim 3, wherein the circuitry is configured to set the boundary in accordance with a distal end position of the subject.

5. The three-dimensional endoscope system according to claim 3, wherein the circuitry is configured to set the boundary in accordance with a distance between an image sensor providing the first and second images and the subject.

6. The three-dimensional endoscope system according to claim 5, wherein the circuitry is configured to calculate a length in a direction orthogonal to a longitudinal axis of the subject in the first image, and determine whether to set the boundary based on the calculated length.

7. The three-dimensional endoscope system according to claim 3, further comprising an endoscope including: an image sensor providing the first and second images; and a treatment instrument channel through which a treatment instrument is to be inserted, wherein the treatment instrument channel includes a sensor to detect passage of the treatment instrument, and the circuitry is configured to set the boundary based on a detection result of the sensor.

8. The three-dimensional endoscope system according to claim 3, wherein the subject is a treatment instrument.

9. The three-dimensional endoscope system according to claim 1, wherein the circuitry is configured to determine presence or absence of movement of a subject appearing in the first image, and, on condition that movement is determined, to generate the third image or, on condition that no movement is determined, to generate the display image including the first image and the second image aligned with each other.

10. A three-dimensional endoscope system comprising:
circuitry configured to capture a first image and a second image having parallax with respect to each other;

perform image processing on the first image and the second image;

determine presence or absence of movement of a subject appearing in the first image; and generate a display image for stereoscopic viewing based on the first image and a third image obtained by replacing a part of the second image with a part of the first image at a corresponding position, wherein the part is an entire periphery of the second image, such that a two-dimensional display image completely surrounds a three-dimensional display image.

11. The three-dimensional endoscope system according to claim 10, wherein the circuitry is configured to:

determine presence or absence of movement of a subject appearing in the first image; and on condition that movement is determined, generate the display image based on the first image and the third image, or on condition that no movement is determined, generate the display image including the first image and the second image aligned with each other.

12. The three-dimensional endoscope system according to claim 10, wherein the circuitry is configured to:

calculate a length in a direction orthogonal to a longitudinal axis of a subject appearing in the first image; and on condition that a boundary is to be set based on the calculated length, set the boundary between the second image and the part of the first image in the third image in accordance with a distance between an image sensor providing the first and second images and the subject.

13. A three-dimensional endoscope system comprising:
circuitry configured to capture a first image and a second image having parallax with respect to each other;

perform image processing on the first image and the second image; and generate a display image based on the first image and a third image obtained by replacing a part of the second image with a part of the first image at a corresponding position;

calculate a length in a direction orthogonal to a longitudinal axis of a subject appearing in the first image; and on condition that a boundary is to be set based on the calculated length, set the boundary between the second image and the part of the first image in the third image in accordance with a distance between an image sensor providing the first and second images and the subject.

14. The three-dimensional endoscope system according to claim 13, wherein the part is an entire periphery of the of the second image, such that a two-dimensional display image completely surrounds a three-dimensional display image.

* * * * *